United States Patent [19]

Kasha, Jr.

[11] Patent Number: 5,565,949
[45] Date of Patent: Oct. 15, 1996

[54] VISUAL FIELD PERIMETRY ON A SMALL COMPUTER SCREEN

[76] Inventor: John R. Kasha, Jr., 9617 Great Hills Trail, Apt. 1012, Austin, Tex. 78759

[21] Appl. No.: 499,852

[22] Filed: Jul. 10, 1995

[51] Int. Cl.⁶ .................................................. A61B 3/02
[52] U.S. Cl. ........................................ 351/224; 351/239
[58] Field of Search ........................... 351/222, 223, 351/224, 237, 239, 243

[56] References Cited

U.S. PATENT DOCUMENTS

| | | | |
|---|---|---|---|
| 4,349,250 | 9/1982 | Gelius | 351/32 |
| 4,798,456 | 1/1989 | Enoch et al. | 351/222 |
| 4,995,717 | 2/1991 | Damato | 351/224 |
| 5,035,500 | 7/1991 | Rovabaugh et al. | 351/226 |

OTHER PUBLICATIONS

Wu, X. et al. Laptop Computer Perimetry for glaucoma screening, Invest. Opthalmol. Vis. Sci. 1991; 32(suppl)810.
Quigley, H. A. et al. Examination Methods for glaucoma Surveys, Arch. Ophthalmol, 1993; 111; 1409–1415.

*Primary Examiner*—Huy Mai

[57] ABSTRACT

A moving and changing fixation point allows visual field perimetry to be performed on the small screen of a laptop computer. A moving fixation point increases the effective area of the screen. A changing fixation point maintains the attention of the user and provides a method of monitoring fixation.

2 Claims, 9 Drawing Sheets

```
Kasha EyeWare Version: 1
Name: Barry, B
Number: 222222222
Birth Date: 11-11-40
Date: 7-14-1995
Time: 9:38:56
Pupil Size: 52
Eye: Right (O.D.)
Screening: Related
Fixation: Moving
Test Time: 60 minutes
Fixation Checks: 7
Fixation Checks Seen: 0
Targets Displayed: 12
```

```
                          0
                 0  0  0  0  0
              0  0  0  0  0  0  0
           0  0  0  0  0  0  0  0  0
           0  0  0  0  0  0  0  0  0
     0  0  0  0  0 24 24  0  0  0  0
           0  0  0  0  0  0  0  0  0
           0  0  0  0  0  0  0  0  0
              0  0  0  0  0  0  0
                 0  0  0  0  0
                          0
```

VISUAL FIELD PERIMETRY ON A SMALL COMPUTER SCREEN

BACKGROUND-FIELD OF INVENTION

This invention relates to visual field perimeters, specifically to the use of personal computers as visual field perimeters.

BACKGROUND-DESCRIPTION OF PRIOR ART

The visual field of the human eye is that portion of vision surrounding the central vision. It is sometimes referred to as the peripheral vision. Perimetry is the primary method of assessing a patient's visual field. Perimetry involves fixating a patient's central vision while presenting light stimulus in their peripheral vision. By presenting large numbers of light stimuli throughout the visual field and recording the patient's reaction to these stimuli, a mapping of the visual field may be obtained.

It is particularly important to obtain visual field mappings when diagnosing and treating diseases which affect the visual field like glaucoma. Currently, most visual field mappings are obtained by machines. These machines are called automated visual field perimeters or computerized perimeters. These machines present light stimuli or targets, monitor the central vision fixation, record the reaction to targets, and map the visual field.

Computerized Perimeters

The majority of computerized perimeters are specialized pieces of hardware. They typically consist of a projection area, an embedded controller, an input device for an operating technician, an input device for the patient, and a method of printing results. These machines are built for physician's offices or hospitals. As a result they are, bulky; not portable, and usually require their own room. They are also expensive. Most computerized perimeters cost between $7000 and $23000.

The process and apparatus used by a typical computerized perimeter are described in U.S. Pat. No. 4,349,250 to Gelius (1982). The process outlined in this patent contains the general steps used by most perimeters. These steps include setting up the patient, pretesting for an individual threshold, modifying the program based on this threshold, monitoring fixation, running the test, and displaying results. The process also contains the useful but not completely necessary step of value comparison with standard values. The apparatus detailed in this patent is specialized. Consequently, it is expensive to build and not portable.

Another drawback to most computerized perimeters is the fatiguing nature of the test. In most perimeters a patient is asked to keep their eye fixated on a stationary point for possibly more than 10 minutes. There have been many attempts to alleviate this problem. The majority of these attempts have focused on the duration of the test. Tests with fewer points and more approximations have been developed. Of course, these tests sacrifice accuracy for a reduction in total test time.

Moving Fixation

Another method introduced to reduce the fatiguing nature of computerized perimetry is a moving fixation point. A moving fixation point means that the eye would also be able to move which would significantly reduce fatigue.

In U.S. Pat. No. 5,035,500 to Rorabaugh et al. (1991) a mechanism is described which allows movement of the fixation point in a visual field test. Although this mechanism may be useful in reducing test fatigue, it suffers from a number of other problems. First of all, the hardware described in this patent is highly specialized. It therefore follows that this equipment will be expensive and not portable.

Secondly, the perimeter described in this patent uses blind spot monitoring as its method of fixation control. Blind spot monitoring involves placing a target stimulus in a patient's blind spot periodically. If the patient sees the target in the blind spot it is assumed that the patient has lost fixation. If the patient does not see the target in the blind spot it is assumed that fixation has been maintained.

There are two problems with blind spot monitoring. The first problem is encountered with blind spot monitoring in general. If a patient has a large visual field defect near or surrounding the blind spot it is difficult to locate the blind spot. It is also not necessarily valid to assume that a blind spot target not seen means that fixation was maintained. The blind spot target may have fallen in the visual field defect.

The second problem encountered with blind spot monitoring results from its use with a moving fixation point. Since the blind spot is located 15 degrees from a patient's central vision, it must be possible to place a blind spot target 15 degrees from the fixation point no matter where it is on the screen. This means that is not possible to use a moving fixation point and blind spot monitoring on a small screen.

A third problem with the mechanism described in U.S. Pat. No. 5,035,500 to Rorabaugh et al. (1991) is the way in which targets are placed in relation to the fixation point. In fact, they are not actually placed. Instead, a number of targets at fixed locations from the fixation point are moved as a group with the fixation point. When a target is illuminated its actual location in the visual field of the eye is calculated. As a result, this method does not produce a uniform field of targets in the visual field of the eye in order to obtain a uniform mapping the target values would have to be interpolated.

Another implementation of a moving fixation point, described in U.S. Pat. No. 4,995,717 to Damato (1991), addresses some of the problems of the mechanism outlined in U.S. Pat. No. 5,035,500 to Rorabaugh et al. (1991). In this implementation a personal computer is used as the visual field perimeter. Using such a general piece of hardware significantly reduces the cost, improves portability, and addresses the first problem of the previous mechanism.

In addition, the implementation described in U.S. Pat. No. 4,995,717 to Damato (1991) uses a different forth of fixation control. As the fixation point moves, the patient is required to keep the fixation point surrounded by a cursor. The cursor is, of course, larger than the fixation point and is controlled by moving the mouse of the personal computer. It is assumed that fixation is maintained while the cursor is surrounding the fixation point. It is assumed that fixation is lost when the cursor is no longer surrounding the fixation point. This method of fixation control avoids the problems of the previous mechanism that were introduced by blind spot monitoring.

Although this implementation has advantages over the previous mechanism it also has problems. First of all, as with the previous mechanism, targets are placed at fixed locations with respect to the fixation point. They are then moved as a group with the fixation point. Again, this procedure results in a nonuniform mapping of the visual field.

Secondly, the method of fixation control requires that the mouse be moved continuously with the fixation point. Such movement of the mouse may be difficult for disabled or elderly people. Also, in this implementation, the patient responds to light stimulus by clicking a mouse button. As a result, test performance may be affected by the patient's ability to coordinate two manual activities involving the mouse.

Laptop Computers

The use of a personal computer as a visual field perimeter can significantly reduce the cost and increase the use of this important diagnostic tool. In the form of a laptop, the most portable personal computer, visual field perimeters can easily move from physician's offices and hospitals to schools, nursing homes, or even third world countries. Wu et al. (1991) described the use of a laptop computer for glumcoma screening. Quigley et al. (1993) detailed the usefulness of such a system in field tests in East Africa.

Although the perimeters described by Wu et al. (1991) and Quigley et al. (1993) were helpful in screening people for glaucoma, they were less sophisticated and useful than the tests used by most computerized perimeters.

A number of factors have prevented visual field tests of the type used by most computerized perimeters from being adapted to laptop computers. Foremost among these factors is the small screen size. Although the screen size of laptop computers has increased over the years it is likely that the screen size will always be limited by the overall size of the machine itself.

Another factor limiting the use of laptops as perimeters has been the quality of their screens. Until recently screens of the quality capable of animation were not readily available.

OBJECTS AND ADVANTAGES

Accordingly, several objects and advantages of my invention are:

(a) to provide a visual field perimeter at a lower cost;

(b) to provide a visual field perimeter that can easily be ported;

(c) to provide a visual field perimeter with a test that is less fatiguing;

(d) to provide a visual field perimeter test that can be performed on small screens.

DRAWING FIGURES

Figure 1:
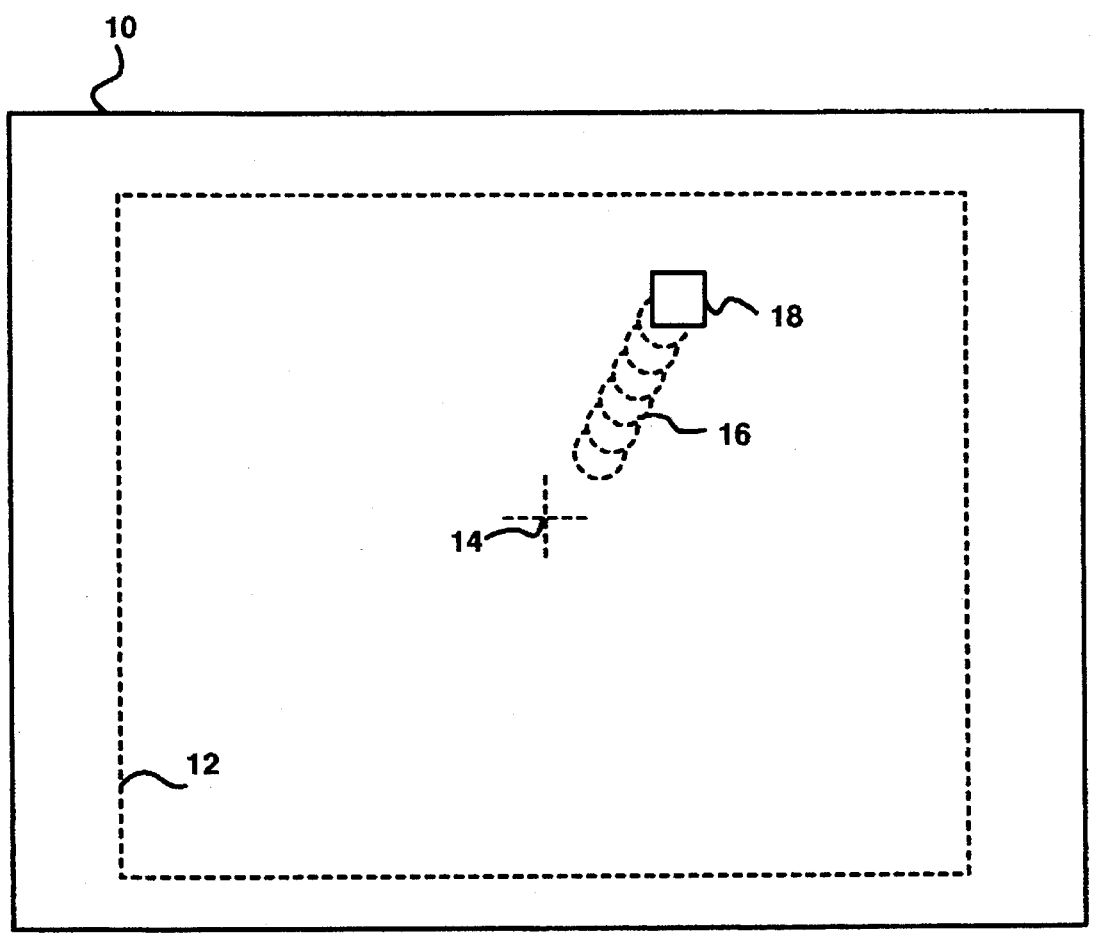
FIG. 1 shows a moving fixation point changing from a circle to a square.

| Reference Numerals In Drawings |
| --- |
| 10 computer screen |
| 12 bounding box |
| 14 center of the screen |
| 16 previous path and shape of fixation point |
| 18 fixation point currently seen on the screen |
| 20 target |
| 22 laptop computer |
| 24 printer |
| 26 mouse |
| 28 hood and eyepiece apparatus |

Figure 2:
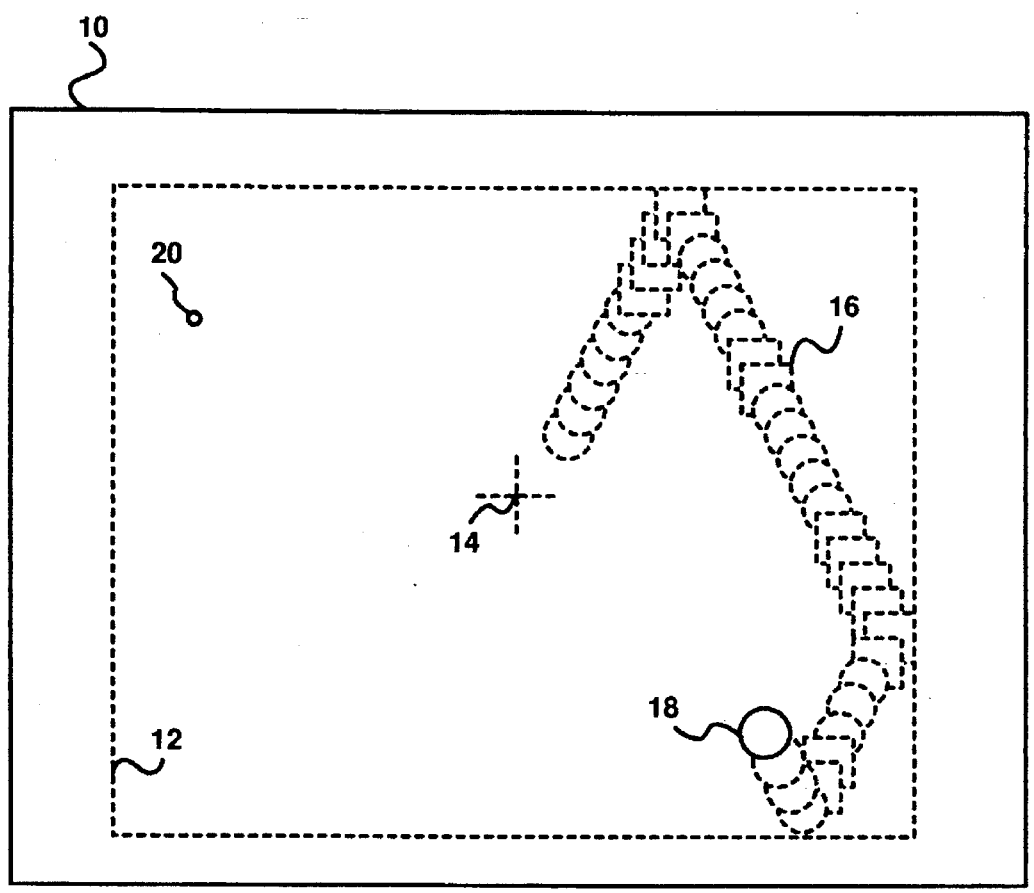
FIG. 2 shows how a target is presented with a moving and changing fixation point.

DESCRIPTION—FIGS. 1 and 2

A preferred embodiment of a moving and changing fixation point is illustrated in FIG. 1. The eye should be located at a known distance from a screen 10 and perpendicular to the plane of the screen at a center of the screen 14. Center of the screen 14 is drawn with dashed lines to indicate that it does not actually appear on screen 10.

The eye should be looking at a fixation point 18. As the fixation point moves, the eye should follow. The movement of fixation point 18 is depicted by showing the previous fixation points along previous path 16 with dashed lines. Note that previous path 16 is linear and diagonal. Thus, the movement of the fixation point is linear and diagonal.

Also note that the previous shape of fixation point 18 was circular. Therefore the transition from previous path and shape 16 to fixation point 18 shows a change in the fixation point. After such a change in fixation point 18 the patient would be required to press a mouse button. Failure to miss a change in fixation point 18 would be called a loss of fixation.

As fixation point 18 nears the edges of the screen it will encounter a bounding box 12. Bounding box 12 is also drawn with dashed lines because it is not shown on screen 10. Bounding box 12 is the boundary around the area in which fixation point 18 is allowed to move.

The function of bounding box 12 is shown more clearly in FIG. 2. FIG. 2 shows fixation point 18 at some time later than FIG. 1. Previous path 16 of fixation point 18 has reached bounding box 12 on three occasions and bounced from bounding box 12. Note that the angle of reflection of previous path 16 is equal to the angle of incidence.

Also shown in FIG. 2 is a target 20. Target 20 is shown within bounding box 12 but it may appear anywhere on screen 10. The angle between target 20 and fixation point 18 corresponds to an angle in the eye that is to be tested. The location of target 20 on screen 10 was calculated based on the location of the eye, the dimensions of screen 10, and the location of fixation point 18.

In static perimetry fixation point 18 would be maintained at screen center 14. The largest angle that could be tested in static perimetry would be the angle from screen center 14 to a corner of screen 10. Note that if fixation point 18 is allowed to move and bounding box 12 is nearly the size of screen 10, an angle from diagonal corners can be tested. Thus the movement of fixation point 18 allows angles twice as large to be tested in any direction, effectively quadrupling the size of screen 10. In other words, a screen four times larger than screen 10 would be required to perform static perimetry and test the same size angles. If target 20 is seen by the patient then they should press a mouse button to signal that target 20 was seen. Note that in the preferred embodiment fixation point 18 will not change shape while a target is being shown. There is no overlap of target stimulus and fixation change.

PROGRAM OPERATION—FIGS. 3–6

Figure 3:
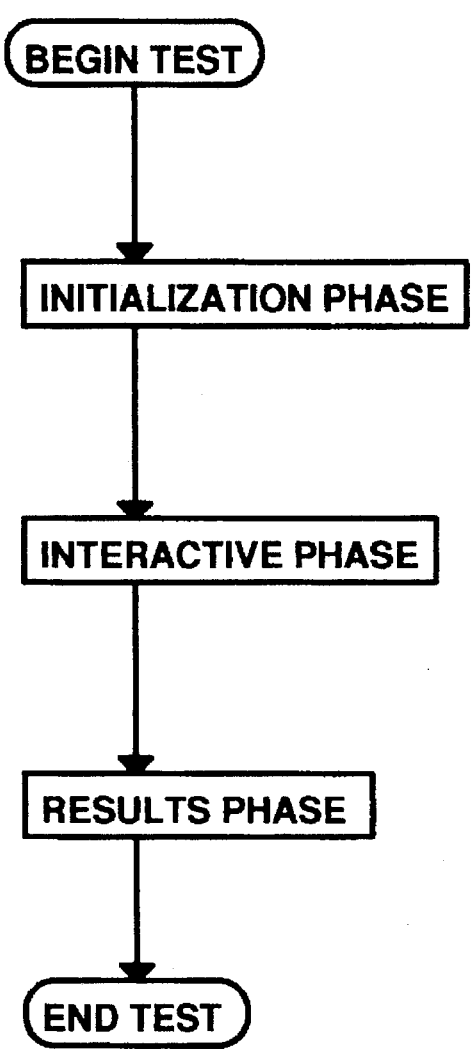
FIG. 3 is a flow chart showing the three main steps of the testing software.

The preferred software used to produce a visual field test with a moving and changing fixation point is outlined in FIG. 3. The software is broken into three steps or phases: the initialization phase, the interactive phase, and the results phase.

Initialization Phase

Figure 4:
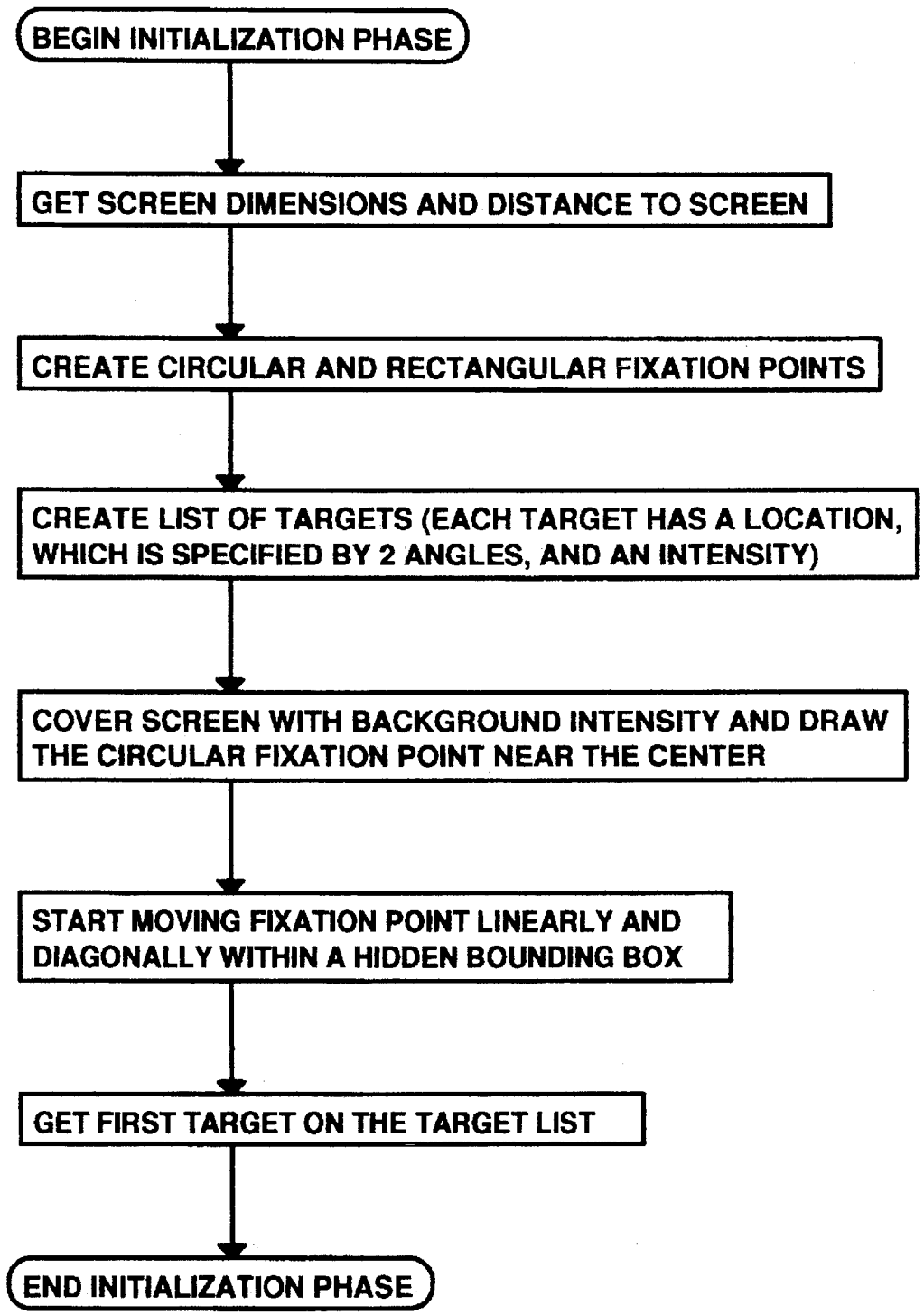
FIG. 4 is a flow chart showing the initialization steps of the testing software.

The initialization phase of the preferred software is outlined in FIG. 4. The first step in this phase is to get the screen dimensions and the distance from the eye to the center of the screen. This information may be recalled from a database or entered at the beginning of each test. This information is required to accurately calculate the position of targets on the screen.

Should the preferred software be used on a conventional cathode ray tube monitor an additional step of setting up the monitor is required. This step would involve adjusting the screen size and light intensity using monitor controls. Currently, the pixels on the screens of laptop computers are fixed so a screen size adjustment is not necessary. Also, screen intensity is less variable on the screens of laptops.

The second step of the initialization phase involves creating the circular and rectangular screen shapes to be used as fixation points. These may be bitmaps.

Similarly a list of targets is created for the type of test selected. All targets have the same shape. Targets also have a location and intensity. The target locations are initially set by specifying two angles. The first angle is the angle from the fixation point to the target from the eye. The second angle is the angle from the horizontal of the plane perpendicular to the line extending from the eye to the fixation point. These angles specify the locations in the eye's visual field that are to be tested and are independent of the screen or fixation point location. The intensity of targets is also set.

The number of targets, their locations and the intensities specified for each target are dependent on the test strategy and screening type. An example strategy is a test of a 30 degree field with targets on the axes, and spaced 6 degrees apart. Such a strategy would have 72 targets. Example screening types would be full-threshold and threshold-related. In a full-threshold test, setting initial intensities to the values of a previous test would help decrease test time. In a threshold-related test, setting the intensities to values expected for a "normal" field would be required.

The next step is to prepare the screen for perimetry. This is done by painting the entire screen with the background intensity or color. The initial shape of the fixation point is also dram on top of the background color near the center of the screen.

Movement of the fixation point is then begun. This is done by drawing the fixation point shape with the background color at the previous location, moving the location, and drawing the fixation point at the new location with the fixation color. This occurs at timed intervals.

The change in location of the fixation point is accomplished by calculating values from the equation of a line. The slope of the line is set so as to move the fixation in a diagonal fashion.

A bounding box is created within the screen limits to be an invisible boundary for the movement of the fixation point. The purpose of the bounding box is to prevent the user from anticipating when the fixation point will change directions, thus giving them another reason to stay focused on the fixation point.

The final step in the initialization phase is getting the first target of the target list. This first target is needed to begin the target loops of the interactive phase.

Interactive Phase

Figure 5:
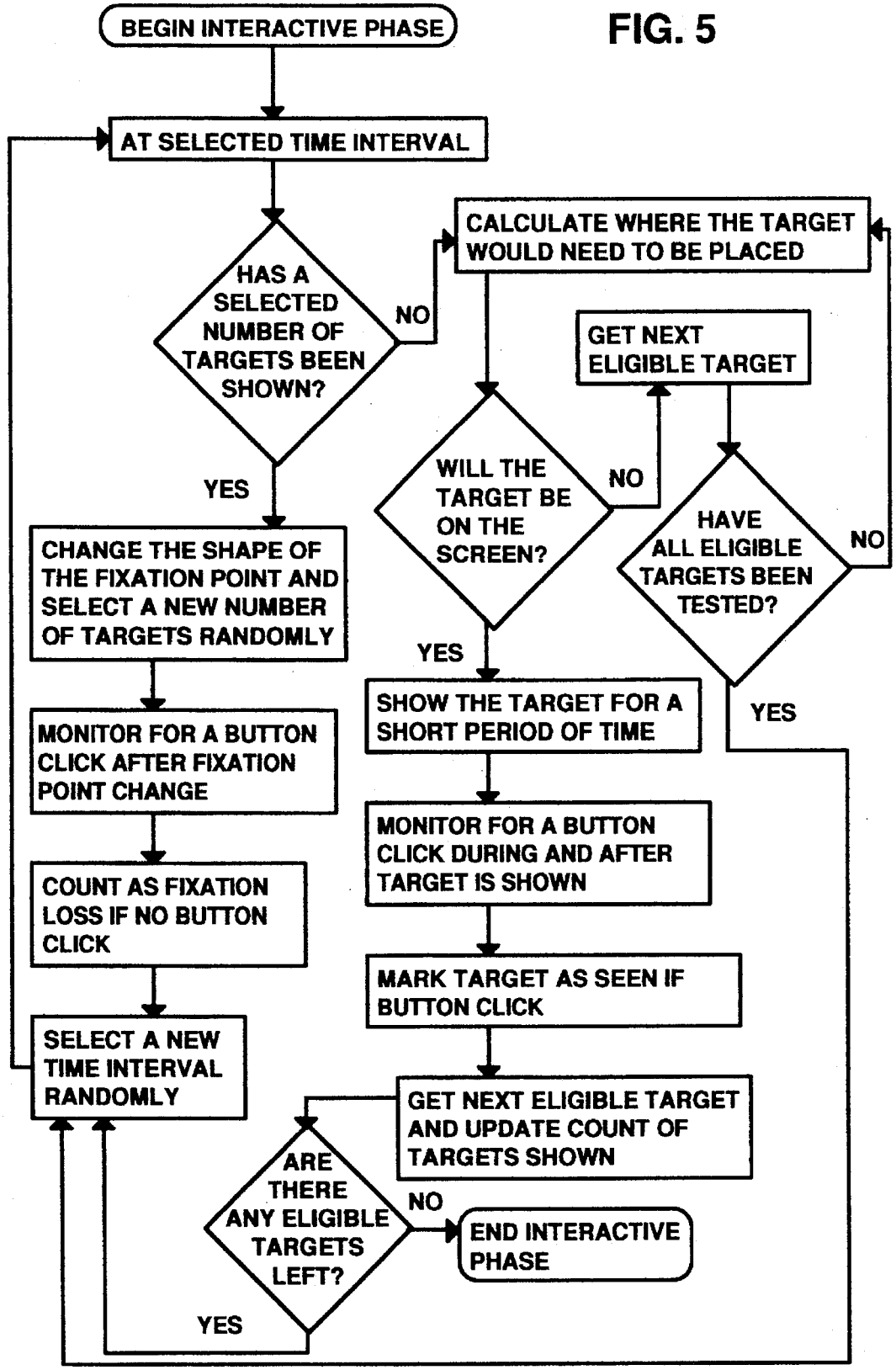
FIG. 5 is a flow chart showing the interactive steps of the testing software.

The interactive phase of the preferred software is outlined in FIG. 5. The interactive phase is where the test stimuli are presented and the user interacts with the software. The interactive phase is an infinite loop through the target list which is broken when all targets have completed their assignments. The loop is controlled by a timer with random intervals.

The loop of the interactive phase is entered at the end of the timed interval. At this point the count of successive targets that were shown is checked. If the count is equal to the previously selected count, the shape of the fixation point is changed. If the shape of the fixation point was a circle it is changed to a square. If it was a square it is changed to a circle. The selected number of successive targets (without a change in fixation) is then reset with a randomly generated number. This check effectively changes the shape of the fixation after a randomly selected number of targets have been presented and prevents the overlap of test stimuli and fixation changes.

After the shape of the fixation point is changed, a mouse button is monitored for a click. If a click is received no fixation loss is recorded. If a click is not received a fixation loss is recorded. Finally, a new interval for the target loop timer is selected and the timer is restarted.

If at the end of the time interval the successive number of targets shown is not equal to the selected count, a calculation is made. This is the calculation of where on the screen the current target would land. This calculation uses the distance from the eye to the center of the screen, the screen dimensions, and the present location of the fixation point on the screen.

Depending on the current location of the fixation point, the target may not land on the screen at all. As a result, a check must be made to determine if the current target may be shown. If it cannot, another eligible target from the target list is obtained. If all other eligible targets have been checked, then no target is shown, the time interval is reset, and the timer is restarted. Essentially, the presentation of targets will be halted until the target can be displayed on the screen.

If all eligible targets have not been checked, the next eligible target becomes the current target and its location on the screen is calculated.

Once an eligible target is found that can be placed on the screen, this target is illuminated at its calculated location. During and after illumination a mouse button is monitored for a click. If a click is received the intensity of the target that was seen is saved with the target information. If a click is not received the target is marked as not having been seen.

The the next eligible target is then obtained and the count of successive targets shown is updated. If an eligible target is found, a new time interval is selected and the timer is restarted. If no eligible targets are left, the interactive phase of the test is completed.

Note that the number of times a target on the target list can be illuminated (is digible) is dependent on the screening type used. If a full-threshold screening type is used, targets may be shown multiple times with different intensities. If a threshold-related test is performed, targets are shown only once.

Results Phase

Figure 6:
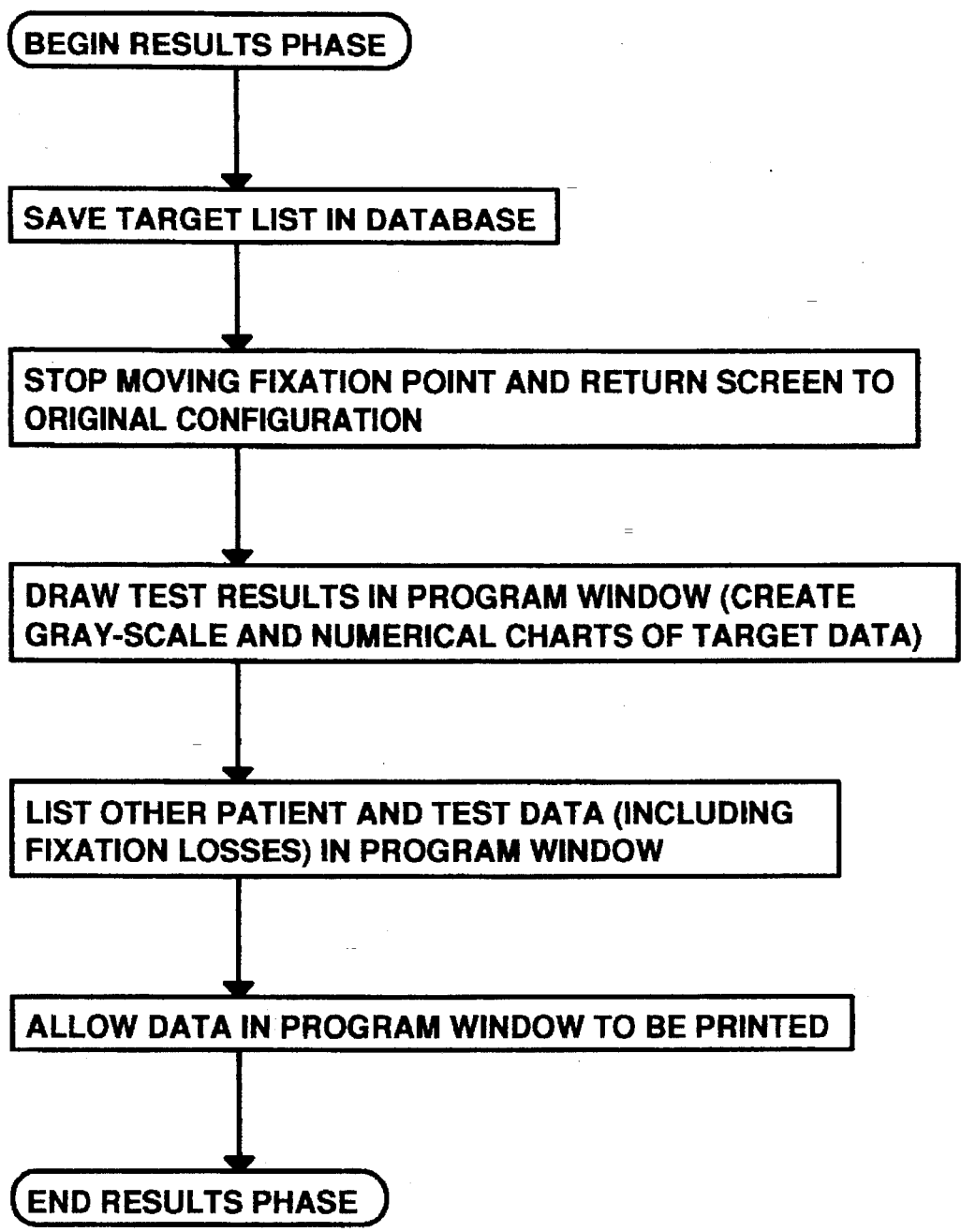
FIG. 6 is a flow chart showing the results steps of the testing software.

The results phase of the preferred software is outlined in FIG. 6. The first step of this phase is to store the target list in the program's database. This list contains the results of the test. The next step is to stop the moving fixation point and return the computer's screen to its original configuration.

With the computer screen restored, the test results can be displayed in the program's window. The results come in two forms. First of all target location and intensity information is presented in gray-scale and numerical chart form. Secondly, patient information and other test information including a fixation loss count are listed.

Finally a mechanism is provided to allow all results information displayed on the screen to be printed.

Figure 7:
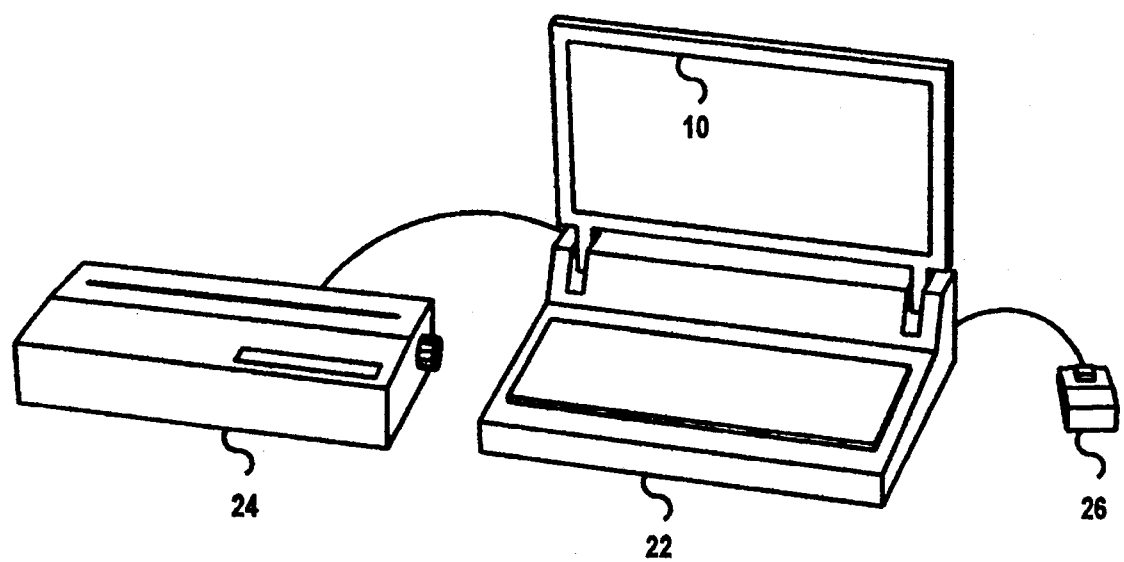
FIG. 7 shows a laptop computer, printer, and mouse.
Figure 8:
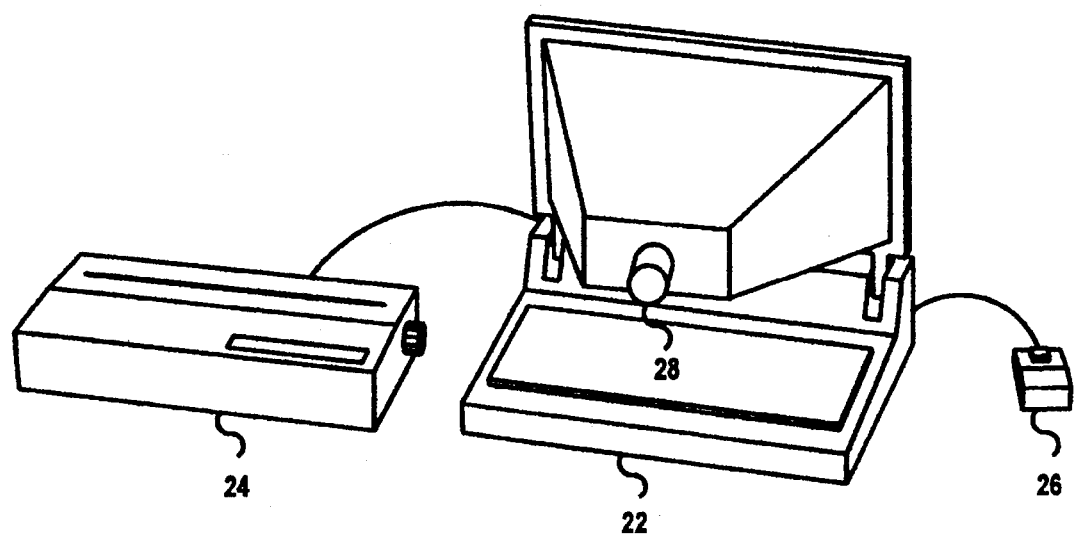
FIG. 8 shows a hood and eyepiece apparatus attached to a laptop computer and a printer and mouse.
Figure 9:
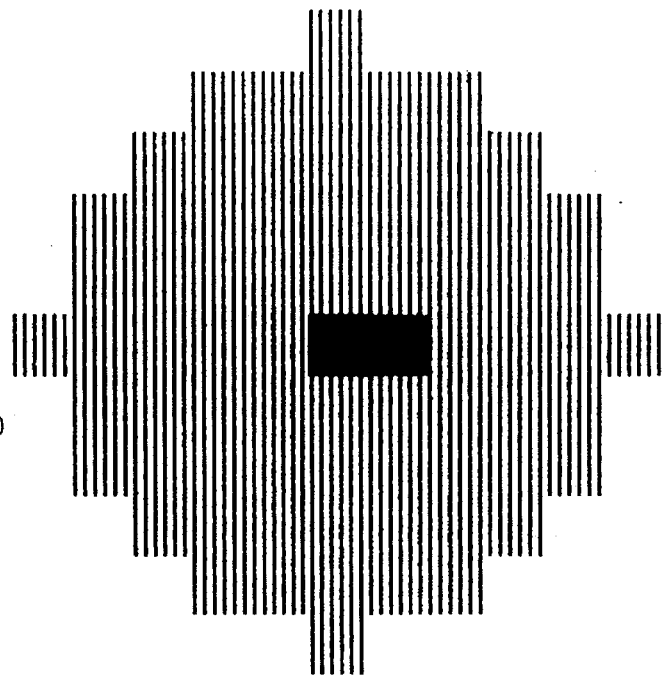
FIG. 9 shows example printed output from a visual field test.
Figure 9:

DESCRIPTION—FIGS. 7 to 9

A laptop computer 22 with computer screen 10 is depicted in FIG. 7. Also shown in this figure is a printer 24 and a mouse 26. The printer 24 is used to prim results of visual field testing. The mouse 24 is the input device used by the patient during testing.

A preferred embodiment of a device to establish the location of the eye with respect to the computer screen 10 shown in FIG. 7 is shown in FIG. 8. A hood and eyepiece apparatus 28 is attached to the laptop computer 22. Also shown in this figure is a primer 24 and a mouse 26.

An example of printed results from a visual field test is shown in FIG. 9. Test information along with target location and intensity information is shown.

SUMMARY, RAMIFICATIONS, AND SCOPE

Accordingly, the reader will see that the invention of a moving and changing fixation point enables visual field perimetry to be performed on the small screen of a laptop computer. These inventions will lower the cost and increase the availability of this important test. Additional advantages of these inventions are:

a visual field test that is less fatiguing than most computerized perimeters;

a portable visual field test that can easily be transported to schools, nursing homes, or even third world countries; and a perimeter that is easy to setup and use.

Although the description above contains many specificities, these should not be construed as limiting the scope of the invention but as merely providing illustrations of some of the presently preferred embodiments of this invention. For example, the moving and changing fixation point may change in color or pattern rather than shape.

Thus the scope of the invention should be determined by the appended claims and their legal equivalence, rather than the examples given.

1. A visual field perimeter which comprises a fixation point; a two-dimensional planar area with finite dimensions; means for fixating the eye with respect to said two-dimensional planar area; discrete targets placed momentarily on said two-dimensional planar area at locations calculated from predefined angles, the location of the eye with respect to said two-dimensional planar area, the dimensions of said two-dimensional planar area and the location of said fixation point; means for moving said fixation point in said two-dimensional planar area so as to maximize the said predefined angles that may be tested in said two-dimensional planar area wherein said predefined angles are angles between the discrete targets and the fixation point with respect to the eye; means for noticeably changing said fixation point so as to maintain the attention of the patient; input means operable by said patient so as to register whether or not said patient sees said noticeable change in said fixation point; input means operable by said patient so as to record whether or not said patient sees each of said discrete targets; and means for recording the relative locations of said discrete targets and whether or not said discrete targets were seen by said patient.

2. A device according to claim 1 wherein an invisible bounding box delimits the area in which said fixation point is allowed to move.

\* \* \* \* \*